(12) United States Patent
Saglimbeni et al.

(10) Patent No.: US 7,068,356 B2
(45) Date of Patent: Jun. 27, 2006

(54) SECURITY IMAGING SYSTEM

(75) Inventors: Anthony Saglimbeni, Centerbrook, CT (US); Henry F. McInerney, Centerbrook, CT (US); Rakesh Vig, Centerbrook, CT (US); Peter Miller, Centerbrook, CT (US)

(73) Assignee: Sun Chemical Corporation, Fort Lee, NJ (US)

( * ) Notice: Subject to any disclaimer, the term of this patent is extended or adjusted under 35 U.S.C. 154(b) by 277 days.

(21) Appl. No.: 10/442,221

(22) Filed: May 20, 2003

(65) Prior Publication Data

US 2003/0218739 A1   Nov. 27, 2003

Related U.S. Application Data

(60) Provisional application No. 60/382,294, filed on May 20, 2002.

(51) Int. Cl.
*G06K 9/74*  (2006.01)

(52) U.S. Cl. .......................................... 356/71; 283/81
(58) Field of Classification Search .................. 283/81, 283/85, 92, 101; 356/71; 250/556
See application file for complete search history.

(56) References Cited

U.S. PATENT DOCUMENTS

| | | | |
|---|---|---|---|
| 5,095,210 A | | 3/1992 | Wheatley et al. |
| 5,485,312 A | | 1/1996 | Horner et al. |
| 5,753,511 A | | 5/1998 | Selinfreund |
| 5,885,677 A | | 3/1999 | Gosselin et al. |
| 6,165,609 A | * | 12/2000 | Curatolo ................ 428/343 |
| 6,232,124 B1 | | 5/2001 | Selinfreund |
| 2003/0194052 A1 | * | 10/2003 | Price et al. ............. 378/45 |

\* cited by examiner

*Primary Examiner*—Layla G. Lauchman
(74) *Attorney, Agent, or Firm*—Kelley Drye & Warren LLP (57) ABSTRACT

Method and system for detecting authenticate products based upon alteration of emission characteristics due to interaction of the emissions with the product and the container.

29 Claims, 5 Drawing Sheets

Figure 1

Backside of label with nine (9) dyes applied.

Image through plastic on Empty Bottle

Fig. 5

Through JW Red

Fig. 6

Through JWB

Fig. 7

Through Pepsi

Fig. 8

Through RC

Fig. 9

SECURITY IMAGING SYSTEM

RELATED APPLICATIONS

This application claims the benefit of U.S. Provisional Application Patent No. 60/382,294, filed May 20, 2002, from which priority is sought and the disclosure of which is herein incorporated by reference.

BACKGROUND OF THE INVENTION

1. Field of the Invention

The present invention generally relates to system for authenticating products based upon measuring anticipated changes in absorption, reflection, or emission of authentication materials due to the physical characteristics of a genuine product or product package. More particularly, the present invention provides for a system for authenticating products based upon an expected differential effect in absorption, reflection or emission with respect to a defined plurality of authentication materials when the absorption, reflection and/or emission of the same are measured across one material versus another. Such system may employ a plurality of authentication materials applied to the back of a product label to produce a fingerprint when the absorption, reflection and/or emission of the authentication materials are measured across a portion of the product or product packaging.

2. Background of the Invention

U.S. Pat. No. 5,753,511 discloses an automated method of developing a database to store information for fingerprint-type analysis. The usefulness of the measurement of the effect of interaction of light-emitting materials within products with other components, such as neutral spirits, vodka, tequila, soft drinks and infant formula, in authenticating genuine product is disclosed. A fingerprint, referring to the light emission intensity from a light-emissive compound in combination with a liquid sample of a product, is used to authenticate the product (Col. 4, Ln. 23–29). There is taught a method for determining the relative amounts of key ingredients in a product by exposing the products to selected light-emissive compounds present in a light-emissive compound. Bandpass and cutoff filters are used to isolate excitation wavelengths from emission spectra due to light emission from the sample.

U.S. Pat. No. 6,232,124B1 similarly discloses measuring light emission from light emissive materials interacting with key elements in a product for the purpose of authenticating the product. The patent claims a method for determining relatedness of a sample to a standard known to be authentic or known to have at least one selected characteristic of authentic material that requires combining a sample with at least one light-emissive compound to form a sample mixture, and irradiating the same to develop a fingerprint.

Systems such as described in U.S. Pat. Nos. 5,753,511 and 6,232,124 permit products such as water, beverages and liquid pharmaceuticals to be fingerprinted using dyes such as fluorescent dyes to determine authenticity when compared to a side by side trial with the authentic product. For comparison purposes, however, samples must often be shipped to an appropriately equipped laboratory. U.S. patent application Ser. No. 09/428,704 commonly assigned, teaches in field testing, may be performed by placing the fluorescent dyes on a microchip. The microchips may be placed into the product and compared to an original in the field for authenticity testing. This provides an enhanced portability to authenticity testing.

U.S. patent application Ser. No. 09/556,280, likely commonly assigned, provides for tracking of the origin of a container and/or authentication of a container using a emission detection device and a printer to print security dyes on the label of a product. The dyes used to mark the container provide a security feature that may be used to determine product authenticity and origin of manufacturing (track and trace). Such system, however, is less than fool proof as the marks may be removed by a skilled artisan.

There remains a need for improved methods for permitting portable product finger printing.

DEFINITIONS

"Authentication Material" refers to a material used to authenticate, identify or mark a product. Among other physical properties, an authentication material may demonstrate different absorption, reflection, or emission upon exposure to an excitation source.

An "Emission profile" can include, but is not limited to, emission intensity and time of relative emission. Analysis of the emission intensity or time of relative emission can be done as described herein and by other methods known to one of ordinary skill in the art. Other emission properties measurable by one of ordinary skill in the art (e.g. emission half-life, emission decay characteristics) are also embraced in the term emission profile.

"Fingerprint" refers to the data set of absorption, reflection, or emission intensity from an authentication material in combination with the product to which it is affixed or intermingled, as measured through a particular media, including media comprising or surrounding the product such as its container. Accordingly, for example, the same product in a different translucent container, different products in the same translucent container, and different products in different translucent containers can all have different fingerprints with respect to one or more authentication materials. A "fingerprint profile" is an assembly of fingerprints.

"Light-Absorbing Compounds": compounds that absorb light in response to irradiation with light. Light absorption can be the result of any chemical reaction known to those of skill in the art.

"Light-Changeable Material": a material that absorbs, reflects, emits or otherwise alters electromagnetic radiation directed at the same. By "light-changeable compound" it is meant to include, without limitation, "light-sensitive", "light-emissive" and "light-absorbing" compounds, as defined below.

"Light-emissive materials" refers to compounds and other materials that are involved in light emission in response to irradiation with light of a different wavelength. Light emission of interest can be a result of phosphorescence, chemiluminescence, or, fluorescence or polarized fluorescence. "Light emissive compounds," includes materials having one or more of the following properties: 1) they are a fluorescent, phosphorescent, or luminescent, 2) interact with components of the sample or the standard or both to yield at least one fluorescent, phosphorescent, or luminescent compound; or 3) interact with at least one fluorescent, phosphorescent, or luminescent compound in the sample, the standard, or both to alter emission at the emission wavelength. The emission wavelength can be any detectable wavelength including visible, infrared (including near infrared), and ultraviolet. Light, as used herein, likewise can be of any wavelength. Light-emissive compounds also include compounds that cause, or interact with components of the standard or sample to cause, or alter, Raman Scatter at a scatter or emission wavelength. The Raman effect occurs when light from a strong source (typically a laser) interacts with a material. Most of the light is absorbed or scattered without wavelength change but some of the light is scattered into other wavelengths (the Raman scatter).

"Light-Sensitive Material": a material capable of being activated so as to change in a physically measurable manner, upon exposure to one or more wavelengths of light.

For the purpose of the rest of the disclosure it is understood that the terms as defined above are intended whether such terms are in all initial cap, or not.

SUMMARY OF THE INVENTION

The present invention provides for a system for authenticating products based upon measuring anticipated changes in absorption, reflection, or emission of authentication materials due to the physical characteristics of a genuine product or product package. More particularly, the present invention provides for a system for authenticating products based upon an expected differential effect in absorption, reflection or emission with respect to a defined plurality of authentication materials when the absorption, reflection and/or emission of the same are measured across one material versus another.

In a preferred embodiment, a plurality of authentication materials, more preferably light-sensitive materials, more preferably light-changeable materials, more preferably light-absorbing, light-reflective, or light-emissive materials, is applied to the back of a product label to produce a fingerprint. Preferably, more than one such material is applied to the back of the label to allow multiple assessments of absorption, emission, reflection etc., at one time. The label is then preferably place against the side of the product to which it is to be applied. Preferably, the authentication material is such that the material possesses or displays (such as emission of a light wavelength) at least one property that can be measured from the non-back side of the label. More preferably the authentication material is of such properties (such as intensity of emission) that such properties can be detected through the product and/or product container. When the label is applied to a product container, it is preferred that the container be of such construct (such as translucent) such that it does not interfere with excitation wavelengths impinging on the authentication material, and likewise does not interfere with the read of properties of authentication material through the container. Likewise, any change of property with respect to the authentication material, preferably, can be read through the product, and in a preferred embodiment such read through the container is dependent upon the product in the container. As would be recognized by one of ordinary skill in the art, the product, product container and the particular authentication material preferably should be chosen allow excitation of the authentication material from outside the product container, and measurement of the response of the authentication material to the excitation form outside the product container.

A preferred label may comprise a plurality of authentication materials, such as light-emitting materials, on its back (the portion typically in contact with the product or container housing the product).

The label may then be placed onto a bottle that contains a product, such as cola or alcohol. An source capable of exciting one or more to the authentication materials may be used. Preferably more than one of such dyes would be excited by the source such that multiple changes can be registered with respect to the authentication materials such that a relative value may be obtained, for example relative fluorescent units. A device capable of both emitting the excitation source and receiving transmission of any response, such as increase in fluorescence, would be advantageous in that it would permit ease of detection of authenticity. The relative fluorescent units, etc. determined through the product acts as a fingerprint of the product authenticity, the product itself, and/or its container typically affecting such reads. Software may be used for example to recognize pre-selected patterns, and statistical software may be used to calculate when the product is non-authentic. Transmission and reading functions may be incorporated into a single device, such as the Verigard 300.

As such the present invention permits the technology of portable product fingerprinting to be transferred to the inside of a label. The label may then be applied against the side of the product. Multiple authentication materials, such as infrared dyes, are preferred as they allow an array of emissions to pass through the product.

When the authentication material, such as light-emissive authentication materials, are used, the detected profiles, such as the light-emissive profile, can be used to determine several factors, for example: (1) serial number determining the origin of the container; (2) if the container is authentic; (3) if the contents are authentic; (4) may act as a measure of safety when imaging the contents of beverage, water sample, or a pharmaceutical before purchase or drinking. The present invention therefore provides in its embodiments a significant advance in the areas of product tracking, authenticity and consumer safety.

In one embodiment there is disclosed, a method for determining the authenticity of, or tracking, a product housed in a container having a label attached thereto having a plurality of limit-emitting materials on the attached side, the method comprising: (a) exciting one or more of the light-emitting materials through the container and the product; (b) monitoring one or more of the emitted wavelengths of light generated in response to the excitation; and (c) comparing the emission profile obtained against a standard fingerprint characteristic of an authentic product housed in an authentic container. One aspect of such embodiment may entail monitoring a plurality of emitted wavelengths.

In another embodiment, there is disclosed a method for determining whether packaging housing a product is authentic, the packaging having a label attached thereto, the label having a plurality of light-emitting materials on the attached side, the method comprising: (a) exciting one or more of the light-emitting materials through the container but not through the product; (b) monitoring one or more of the emitted wavelengths of light generated in response to the excitation; and (c) comparing the emission profile obtained against a standard fingerprint characteristic of an authentic packaging. One aspect of such embodiment may entail monitoring a plurality of emitted wavelengths.

BRIEF DESCRIPTION OF THE DRAWINGS

The accompanying drawings, which are incorporated in and constitute part of the specification, illustrate presently preferred embodiments of the invention, and together with the general description given above and the detailed description of the preferred embodiments given below, serve to explain the principles of the invention.

DETAILED DESCRIPTION OF THE INVENTION

Is would be recognized by one of ordinary skill in the art, a number of authentication materials can be use in the practice of the present invention. Some preferred materials are set forth below in Table 1.

TABLE 1

| Dye Name/No. | Excitation | Emission |
|---|---|---|
| Alcian Blue (Dye 73) | 630 nm | Absorbs |
| Methyl Green (Dye 79) | 630 nm | Absorbs |
| Methylene Blue (Dye 78) | 661 nm | 686 nm |
| Indocyanine Green (Dye 77) | 775 nm | 818 nm |
| Copper Phthalocyanine (Dye 75) | 795 nm | Absorbs |
| IR 140 (Dye 53) | 823 nm | 838 nm |
| IR 768 Perchlorate (Dye 54) | 760 nm | 786 nm |
| IR 780 Iodide (Dye 55) | 780 nm | 804 nm |
| IR 780 Perchlorate (Dye 56) | 780 nm | 804 nm |
| IR 786 Iodide (Dye 57) | 775 nm | 797 nm |
| IR 768 Perchlorate (Dye 58) | 770 nm | 796 nm |
| IR 792 Perchlorate (Dye 59) | 792 nm | 822 nm |
| 1,1'-DIOCTADECYL-3,3,3',3'-TETRAMETHYLINDODICARBOCYANINE IODIDE (Dye 231) | 645 nm | 665 nm |
| 1,1'-DIOCTADECYL-3,3,3',3'-TETRAMETHYLINDOTRICARBOCYANINE IODIDE (Dye 232) | 748 nm | 780 nm |
| 1,1',3,3,3',3'-HEXAMETHYL-INDODICARBOCYANINE IODIDE (Dye 233) | 638 nm | 658 nm |

TABLE 1-continued

| Dye Name/No. | Excitation | Emission |
|---|---|---|
| DTP (Dye 239) | 800 nm | 848 nm |
| HITC Iodide (Dye 240) | 742 nm | 774 nm |
| IR P302 (Dye 242) | 740 nm | 781 nm |
| DTTC Iodide (Dye 245) | 755 nm | 788 nm |
| DOTC Iodide (Dye 246) | 690 nm | 718 nm |
| IR-125 (Dye 247) | 790 nm | 813 nm |
| IR-144 (Dye 248) | 750 nm | 834 nm |

A series of experiments was undertaken to demonstrate that authentication of the product in a bottle could be improved by using the method of the present invention, as well as other advantages could be achieved.

EXAMPLE 1

Figure 1:
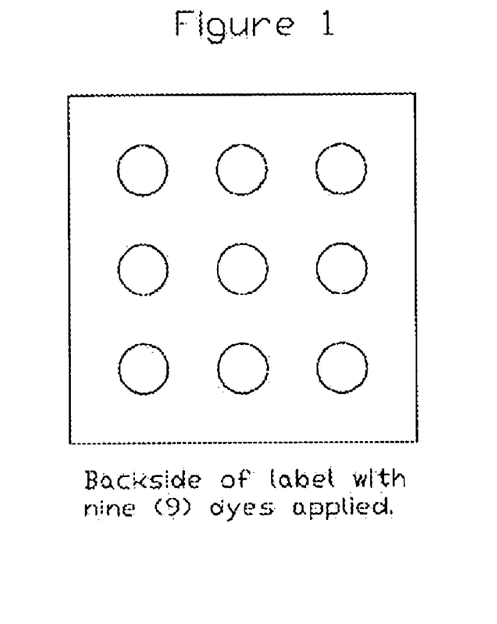
FIG. 1 illustrates a label having nine authentication dyes applied to its backside.
Figure 2:
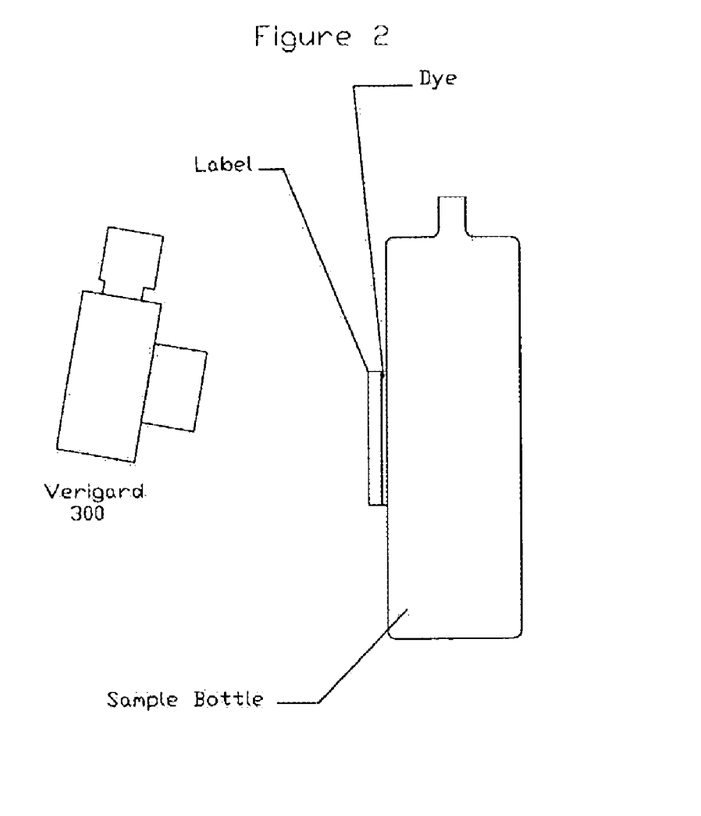
FIG. 2 illustrates a bottle with authentication label applied with authentication occurring by reading a change in the authentication dyes of FIG. 1 across the front of the label.

The dyes were imaged through the label. To address the problem of making security markings resistant to rub off and solvent removal, the near infrared fluorescent dyes were placed under the label and a commercially available security camera (Verigard 300 camera) was used to image the dyes. Nine fluorescent dyes that have an excitation range of 710–735 nm were placed onto an absorbent material (FIG. 1). The label containing the dyes was then placed dye side against the side of a container (FIG. 2). An image of the dyes was then taken with the Verigard 300 camera (reference Veritec U.S. patent application Ser. No. 09/556,280). The Verigard 300 has two light emitting diode power supplies and a sensor that detects light from 740 nm to about 1100 nm. In this experiment the camera provides a means to detect the emission through to the label. The image from the Verigard 300 was then analyzed by exporting the image from the camera and importing it into a software program called Imagequant (Amersham Biosciences; Piscataway, N.J.). Image not shown.

EXAMPLE 2

Figure 3:
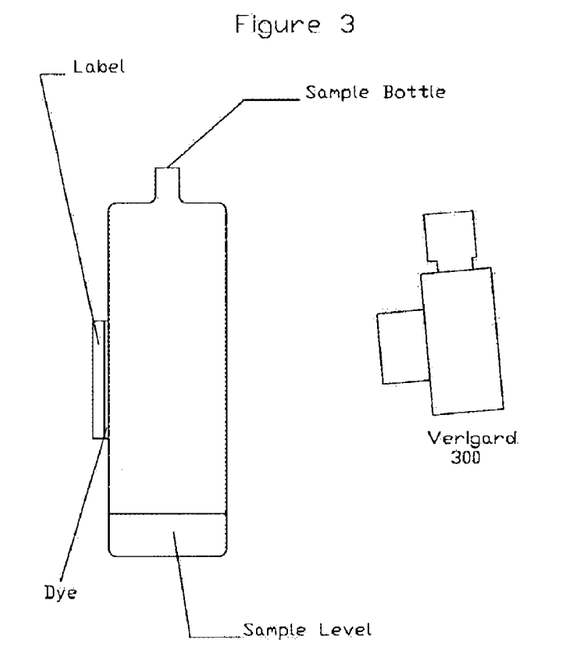
FIG. 3 illustrates a bottle with an authentication label of the present invention applied, with authentication occurring by reading a change in the authentication dyes through a wall of the bottle.
Figure 4:
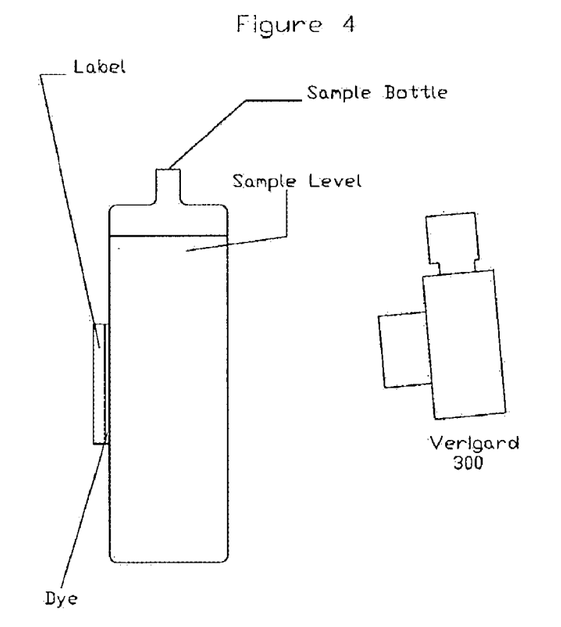
FIG. 4 illustrates a bottle with an authentication label of the present invention applied, with authentication occurring by reading a change in the authentication dyes through a wall of the bottle and through the product.
Figure 5:
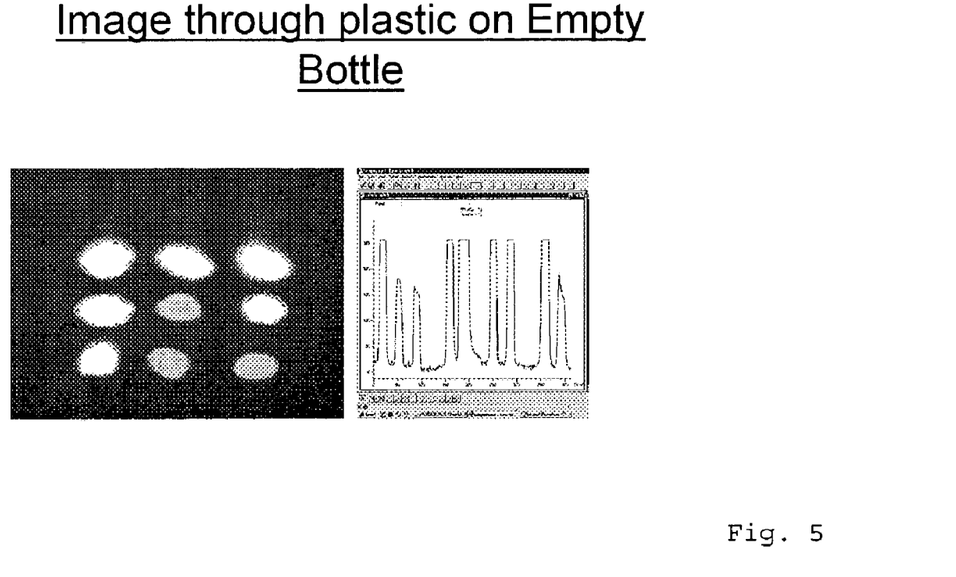
FIG. 5 is an image of, and an Imagequant spectrum analysis of, NIR dyes on a label across an empty plastic bottle.

The second set of experiments was designed to address the question of whether is was possible to image the dyes not only through the label alone (as described by Gosselin and Walfredo U.S. Pat. No. 5,885,677), but also to image the dyes through the container. The dyes were placed onto an absorbent material exactly as described in the first set of experiments. In this experiment the label containing the dyes was placed dye side against the side of the container. An image of the dyes was then taken with the Verigard 300 camera through the empty container (FIG. 3). The image was then exported and analyzed using Imagequant software (shown in FIG. 5). Based on this data it was discovered that the NIR dyes could be imaged through the container.

EXAMPLE 3

Figure 6:
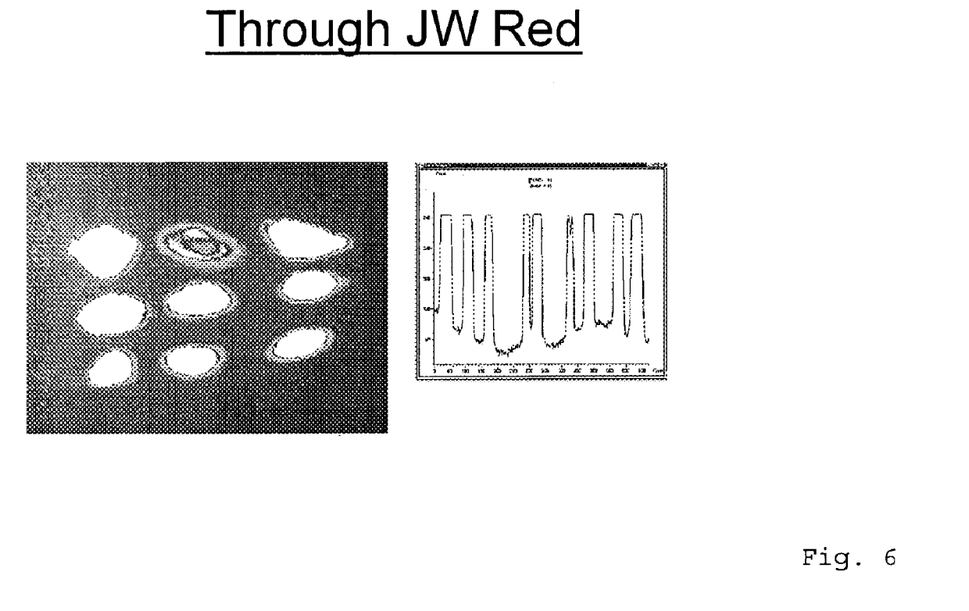
FIG. 6 is an image of, and an Imagequant spectrum analysis of, NIR dyes through a full bottle of Scotch whiskey.

The Dye label system, Lab on a Label, (LOL) was applied to a container full of product. In this set of experiments the dyes were made up and placed on the label as previously described. An image of the LOL label was taken with the Verigard 300 camera through a full bottle of Scotch Whiskey (Johnnie Walker Red Label®). The image was then exported and analyzed using Imagequant software (shown in FIG. 6). Based on this data, it was discovered that the NIR dyes could be imaged through a full container. If the NIR dyes had been placed using a continuous ink jet printer (CIJ) or another printing method then the camera could read a security code on the back of the label. The image would not be visible to the eye but could provide a mark for bottle origin and whether the bottle was authentic.

EXAMPLE 4

Figure 7:
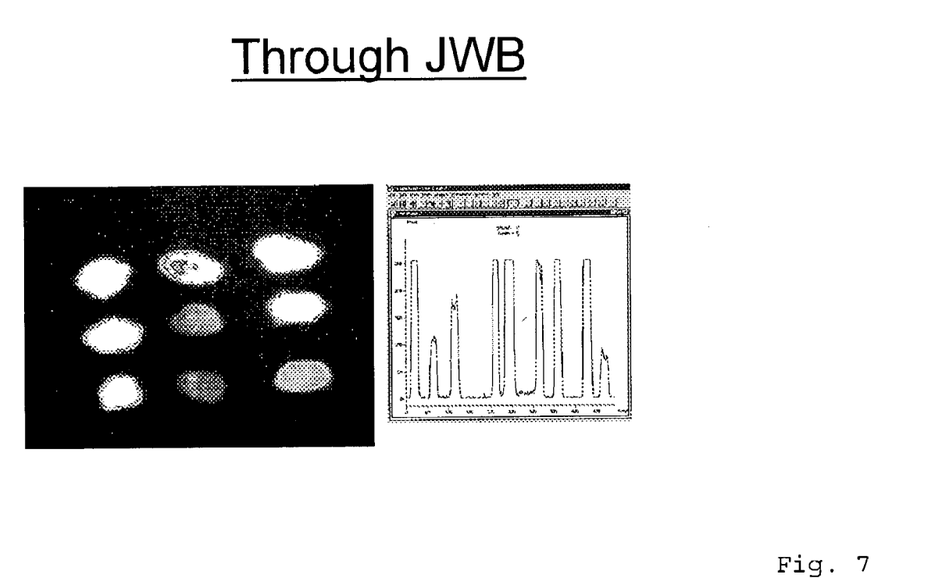
FIG. 7 is an image of, and an Imagequant spectrum analysis of, NIR dyes through a full bottle of another brand of Scotch whiskey.
Figure 8:
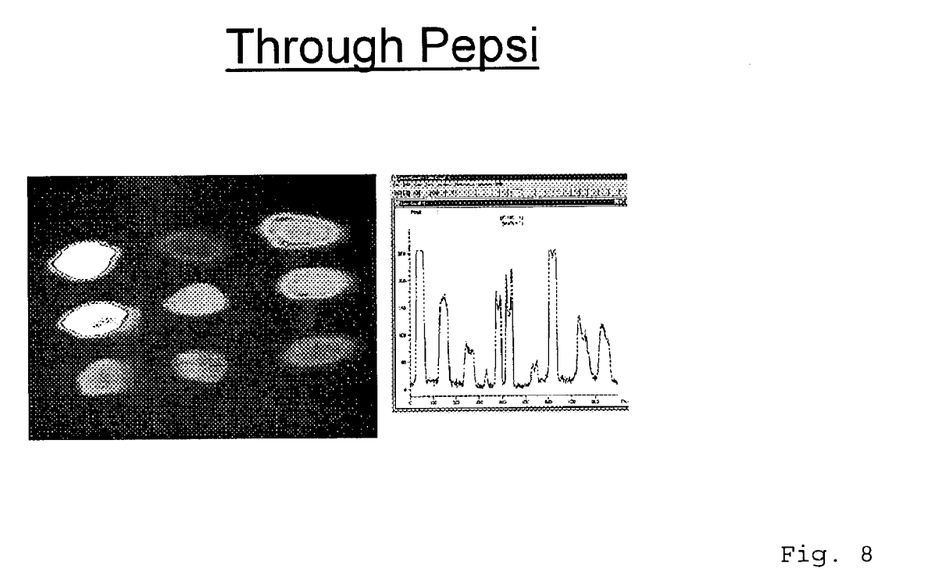
FIG. 8 is an image of, and an Imagequant spectrum analysis of, NIR dyes through a full bottle of cola.
Figure 9:
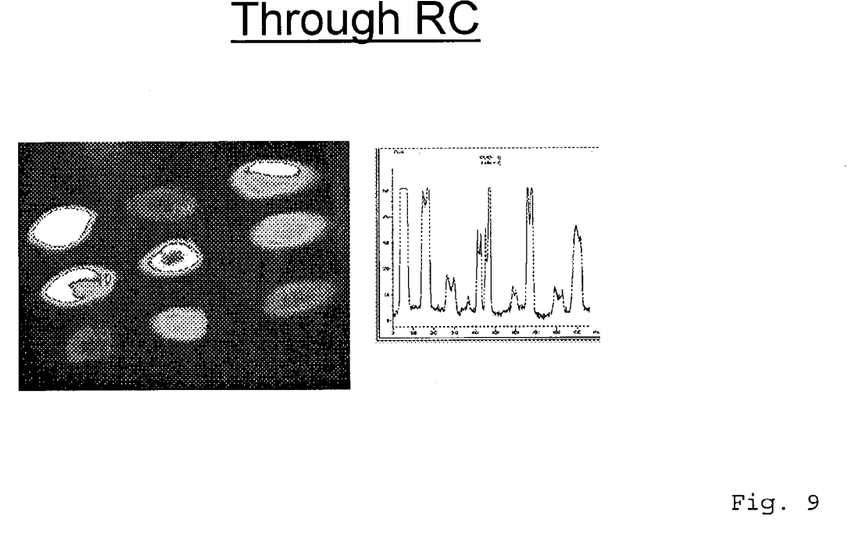
FIG. 9 is an image of, and an Imagequant spectrum analysis of, NIR dyes through a full bottle of another brand of cola.

In this set of experiments the dyes were made up and placed on the label as previously described. An image of the LOL the label was taken with the Verigard 300 camera using the same LOL label as used in the previous experiment. This time the label was applied face against a different but closely related bottle of Scotch Whiskey (Johnnie Walker Black®). The resulting pattern after analysis with Imagequant software detects a difference between the two scotches (FIG. 7). In the same set of experiments is was possible to show with using the same LOL label that the system could differentiate the difference between Pepsi® (FIG. 8) and RC® (FIG. 9) cola when imaged through the container. Such technique could be used to verify the safety of a product or its authenticity.

EXAMPLE 5

Studies were undertaken to determine whether the V-300 can read through opposite side of different labels and to study the variation in the fluorescence of the various dye combinations when placed on the inside of a label and read across the other end of a bottle, either filled with a liquid or empty.

Dye Formulations:

| DYE PAIR CODE NAME | DYE PAIR | RESPECTIVE CONCENTRATIONS (IN μM) |
|---|---|---|
| 1 | 451 + 240 | 50, 125 |
| 2 | 575 + 248 | 75, 62.5 |
| 3 | 240 + 575 | 150, 125 |
| 4 | 575 + 242 | 150, 0.025% (grams/mL) |
| 5 | 451 + 575 | 75, 250 |
| 6 | 661 + 240 | 375, 375 |
| 7 | 240 + 248 | 750, 625 |
| 8 | 575 + 459 | 150, 125 |
| 9 | 575 + 450 | 175, 75 |

The dyes were made up in the concentrations listed above in halo minus varnish (678) and applied using a micropipette. One micro liter was dispensed per spot. The order the dyes were applied is as follows.

| 1 | 2 | 3 |
|---|---|---|
| 4 | 5 | 6 |
| 7 | 8 | 9 |

After the application of the dye pairs, they were allowed to dry for ninety minutes. After drying, various images were taken. The label was affixed to a 24 fluid ounce bottle of Pepsi® and an image was taken across the filled bottle. The bottle was then emptied and an image was taken across the empty bottle. The bottle was then filled with RC Cola® and a third image was taken using the V300 camera. The same Pepsi® label was then taped onto a 1.75 L glass bottle of Johnny Walker Black Label® Whiskey (full) and an image was taken of this across the bottle. Finally, the label was attached to a 1.75 L glass bottle of Johnny Walker Red Label® Whiskey (full).

While the invention has been described with respect to preferred embodiments, those skilled in the art will readily appreciate that various changes and/or modifications can be made to the invention without departing from the spirit or scope of the invention as defined by the appended claims. All documents cited herein are incorporated in their entirety herein.

What is claimed is:

1. A method for determining the authenticity of a product housed in packaging having a label attached thereto, the label having a plurality of authentication materials associated therewith, at least two of said authentication materials eliciting at least one measurably different property upon excitation of the authentication materials by an excitation source, said method comprising the steps of:
    (a) exciting said at least two authentication materials by way of said excitation source directed across said packaging and said product to said at least two authentication materials;
    (b) monitoring said at least one excitation-dependent property of each of said at least two authentication materials after excitation by way of said excitation source;
    (c) developing a relative relationship profile between the at least one excitation-dependent property of each of said at least two authentication materials after excitation by way of said excitation source;
    (d) comparing said relative relationship profile of step (c) with the relative relationship profile characteristic of said at least two authentication materials after excitation by way of said excitation source with respect to a standard for an authentically labeled, authentic product housed in authentic packaging;
    (e) declaring authenticate said product when said relative relationship profile of step (c) corresponds to the relative relationship profile of said standard.

2. The method of claim 1 wherein monitoring step b entails monitoring of a plurality of emitted wavelengths from said authentication material.

3. The method of claim 2 wherein monitoring step b is performed using a monitor positioned to receive said emitted wavelengths after passage of said emitted wavelengths through said product and said packaging.

4. The method of claim 1 wherein monitoring step b entails monitoring changes in absorption elicited by excitation of said authentication materials by said excitation source.

5. The method of claim 1 wherein monitoring step b entails monitoring changes in reflection elicited by excitation of said authentication materials by said excitation source.

6. The method of claim 1 wherein monitoring step b entails monitoring changes in emission elicited by excitation of said authentication materials by said excitation source.

7. The method of claim 1 wherein said authentication material is a light-absorbing compound and the property monitored is a light-absorbing property.

8. The method of claim 1 wherein said authentication material is a light-changeable material and the property monitored is a light-changeable property.

9. The method of claim 1 wherein said authentication material is a light-emissive material and the property monitored is a light-emissive property.

10. The method of claim 1 wherein said authentication material is a light-sensitive material and the property monitored is a light-sensitive property.

11. The method of claim 1 wherein said product is a liquid.

12. The method of claim 1 wherein said packaging is transparent.

13. The method of claim 1 wherein said at least two authentication materials are found inside of said label.

14. The method of claim 1 wherein said at least two authentication materials are found on the on the side of said label attached to said packaging.

15. The method of claim 1 wherein said at least two authentication materials are found on the front side of said label attached to said packaging.

16. A method for determining the authenticity of packaging housing a product, said packaging having a label attached thereto, the label having a plurality of authentication materials associated with the attached side, at least two of said authentication materials eliciting at least one measurably different property upon excitation of the authentication materials by an excitation source, said method comprising the steps of:
  (a) exciting said at least two authentication materials by way of said excitation source directed across said container, but not across said packaging, to said at least two authentication materials;
  (b) monitoring said at least one excitation-dependent property of each of said at least two authentication materials after excitation by way of said excitation source;
  (c) developing a relative relationship profile between the at least one excitation-dependent property of each of said at least two authentication materials after excitation by way of said excitation source;
  (d) comparing said relative relationship profile of step (c) with the relative relationship profile characteristic of said at least two authentication materials after excitation by way of said excitation source with respect to a standard for authentically labeled, authentic packaging;
  (e) declaring authenticate said packaging when said relative relationship profile of step (c) corresponds to the relative relationship profile of said standard.

17. The method of claim 16 wherein monitoring step b entails monitoring of a plurality of emitted wavelengths from said authentication material.

18. The method of claim 16 wherein monitoring step b is performed using a monitor positioned to receive said emitted wavelengths after passage of said emitted wavelengths through said packaging.

19. The method of claim 16 wherein monitoring step b entails monitoring changes in absorption elicited by excitation of said authentication materials by said excitation source.

20. The method of claim 16 wherein monitoring step b entails monitoring changes in reflection elicited by excitation of said authentication materials by said excitation source.

21. The method of claim 16 wherein monitoring step b entails monitoring changes in emission elicited by excitation of said authentication materials by said excitation source.

22. The method of claim 16 wherein said authentication material is a light-absorbing compound and the property monitored is a light-absorbing property.

23. The method of claim 16 wherein said authentication material is a light-changeable material and the property monitored is a light-changeable property.

24. The method of claim 16 wherein said authentication material is a light-emissive material and the property monitored is a light-emissive property.

25. The method of claim 16 wherein said authentication material is a light-sensitive material and the property monitored is a light-sensitive property.

26. The method of claim 16 wherein said packaging is transparent.

27. The method of claim 16 wherein said at least two authentication materials are found inside of said label.

28. The method of claim 16 wherein said at least two authentication materials are found on the on the side of said label attached to said packaging.

29. The method of claim 16 wherein said at least two authentication materials are found on the front side of said label attached to said packaging.

* * * * *